(12) United States Patent
Reigstad et al.

(10) Patent No.: US 7,837,738 B2
(45) Date of Patent: Nov. 23, 2010

(54) JOINT PROSTHESIS AND USE OF SCREW TOOL FOR POSITIONING MEMBERS THEREOF

(75) Inventors: Astor Reigstad, Oslo (NO); Lars Öster, Lidköping (SE)

(73) Assignee: Swemac Orthopaedics AB, Linkoping (SE)

( * ) Notice: Subject to any disclaimer, the term of this patent is extended or adjusted under 35 U.S.C. 154(b) by 387 days.

(21) Appl. No.: 11/884,092

(22) PCT Filed: Feb. 13, 2006

(86) PCT No.: PCT/SE2006/000189

§ 371 (c)(1),
(2), (4) Date: Aug. 9, 2007

(87) PCT Pub. No.: WO2006/088412

PCT Pub. Date: Aug. 24, 2006

(65) Prior Publication Data

US 2008/0065224 A1 Mar. 13, 2008

(30) Foreign Application Priority Data

Feb. 16, 2005 (SE) .................................. 0500353-8

(51) Int. Cl.
*A61F 2/42* (2006.01)
(52) U.S. Cl. .................................. 623/21.11; 623/21.13
(58) Field of Classification Search ............... 623/21.11, 623/21.12, 22.12, 23.24, 23.27
See application file for complete search history.

(56) References Cited

U.S. PATENT DOCUMENTS

| 4,624,673 | A | 11/1986 | Meyer |
| 5,147,386 | A | 9/1992 | Carignan et al. |
| 5,464,407 | A | 11/1995 | McGuire |
| 5,580,352 | A | 12/1996 | Sekel |
| 6,190,416 | B1 * | 2/2001 | Choteau et al. .......... 623/22.12 |
| 6,284,001 | B1 | 9/2001 | Knapp |
| 6,827,722 | B1 | 12/2004 | Schoenefeld |

(Continued)

FOREIGN PATENT DOCUMENTS

EP 1 297 794 A2 4/2003

*Primary Examiner*—Bruce E Snow
*Assistant Examiner*—Melissa Montano
(74) *Attorney, Agent, or Firm*—Tarolli, Sundheim, Covell & Tummino LLP

(57) ABSTRACT

A joint prosthesis has two prosthesis members (2, 3) and each prosthesis member (2, 3) includes a first and a second screw-like member (4, 5) adapted to be screwed onto a respective bone (39, 41, 42). One prosthesis member (2) includes a member (6) having a socket and the other prosthesis member (3) a member (7) having a head. The socket member (6) has a mounting pin (22) insertable into a first hole (10) in the first screw-like member (4) and the head member (7) has a mounting pin (27) insertable into a first hole (11) in the second screw-like member (5). In the first as well as in the second screw-like member (4, 5) there is provided at least one inner second hole (30 and 33 respectively) designed to permit insertion thereinto of a rod (31) of a screw tool (32) in order to secure by screwing the first and second screw-like member (4, 5) respectively, at the respective bone (39, 41, 42). The second hole (30 and 33 respectively) is provided in a bottom (17 and 19 respectively) of the first hole (10 and 11 respectively).

27 Claims, 5 Drawing Sheets

U.S. PATENT DOCUMENTS

| | | |
|---|---|---|
| 2002/0111692 A1 * | 8/2002 | Ralph et al. .............. 623/23.17 |
| 2003/0014054 A1 * | 1/2003 | Huebner ...................... 606/73 |
| 2005/0251264 A1 * | 11/2005 | Katz et al. ............... 623/21.11 |

* cited by examiner

JOINT PROSTHESIS AND USE OF SCREW TOOL FOR POSITIONING MEMBERS THEREOF

FIELD OF THE INVENTION

The present invention relates to a joint prosthesis, comprising two prosthesis members which are adapted to be positioned at different bones at a joint, each prosthesis member including a first and a second screw-like member respectively, which are adapted to be screwed onto the respective bone. One of the prosthesis members includes a member having a socket and the other prosthesis member a member having a head. The socket member has a mounting pin which is insertable into a first hole in the first screw-like member for positioning or locating the socket member thereto and the head member has a mounting pin which is insertable into a first hole in the second screw-like member for positioning or locating said head member thereto. The invention also relates to a screw tool for positioning members of the joint prosthesis.

BACKGROUND OF THE INVENTION

In the publication U.S. Pat. No. 5,147,386 there is described a joint prosthesis having two screw-like members which are mounted or attached to the respective bones to be connected by the prosthesis. The joint consists of a socket and a head, whereby the end of the head member is attached to one of the screw-like members by a press fit. To secure the screw-like members by screwing, there are grooves for a screw tool in outer end surfaces thereof, which means that the grooves will form sharp edges that might harm adjacent tissue, which of course is utterly inappropriate.

SUMMARY OF THE INVENTION

The object of the present invention is to eliminate the problem that the screw-like members of the prosthesis members have outer grooves defining sharp edges. This is arrived at while the prosthesis is provided with the characterizing features of primarily subsequent claim 1.

Since the screw-like members of the prosthesis, within the hole therein for socket and head members respectively, are provided with inner holes which are designed particularly for a screw tool, it is possible to insert the screw tool in the hole in order to attach by screwing the screw-like members to the bone in question and avoid the outer grooves with sharp edges which can cause damages. Since the holes for the screw tool are inner holes, they will be completely covered by the socket and head members of the prosthesis when these members are mounted.

BRIEF DESCRIPTION OF THE DRAWINGS

The invention will be described in more detail below with reference to the accompanying drawings, in which.

DESCRIPTION OF EXAMPLE EMBODIMENTS

Figure 1:
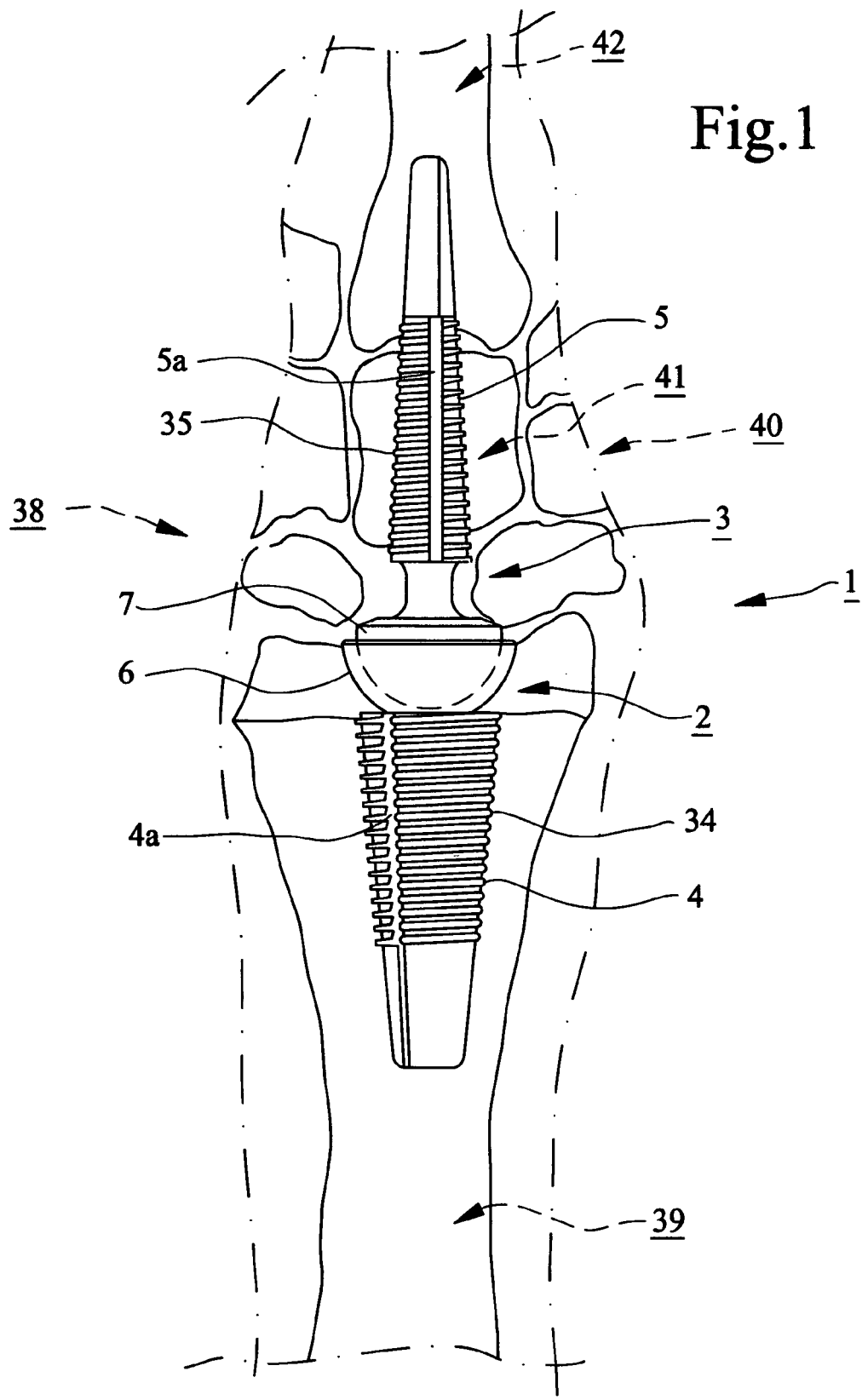
FIG. 1 is a side view of a wrist prosthesis according to the invention as an implant in a wrist.

In the drawings, a wrist prosthesis 1 is shown comprising a first prosthesis member 2 and a second prosthesis member 3. The first prosthesis member 2 includes a first screw-like member 4 and the second prosthesis member 3 a second screw-like member 5. The first prosthesis member 2 further includes a member 6 having a socket and the second prosthesis member 3 a member 7 with a head. Each first and second screw-like member 4, 5 respectively, has a mounting portion 8 and 9 respectively, which at the illustrated embodiment is provided with a first hole 10 and 11 respectively. The first hole 10 in the first screw-like member 4 extends as a depression at a first end edge 12 at which said member 4 has the largest diameter in an axial direction towards a second end edge 13 of said member 4 at which the member 4 has its smallest diameter. The first hole 10 is preferably centered with a geometric center line CL1 extending in the axial direction of the member 4.

The first hole 11 in the second screw-like member 5 extends as a depression at a first end edge 14 at which said member 5 has the largest diameter in an axial direction towards a second end edge 15 of said member 5 at which the member 5 has the smallest diameter. The first hole 11 is centered with a geometric center line CL2 extending in the axial direction of the member 5.

The first hole 10 in the first screw-like member 4 has its largest diameter at the first end edge 12 and its side walls 16 are conical, whereby its smallest diameter is at the bottom 17 of the hole 10, i.e. the first hole 10 tapers conically towards its bottom 17.

The first hole 11 in the second screw-like member 5 has its largest diameter at the first end edge 14 and its side walls 18 are conical, whereby its smallest diameter is at the bottom 19 of the hole 11, i.e. the hole 11 tapers conically towards its bottom 19.

The socket member 6 has a socket 20 which defines a concave joint surface 21. From the outer side of the socket 20, a mounting pin 22 extends in an axial direction. The mounting pin 22 has an axial outer side 24 which tapers conically towards its end edge 23. The shape and dimension of the mounting pin 22 and the shape and dimension of the first hole 10 in the first screw-like member 4 are chosen such that they can form a press fit by compression in an axial direction, i.e. a connection which through compression permits attachment of the socket member 6 and the first screw-like member 4 to each other.

The head member 7 has a substantially spherical head 25 which forms a convex joint surface 26 of such shape that it fits into the joint surface 21 of the socket member 20 such that said joint surfaces 21, 26 can glide against each other and make the joint flexible. A mounting pin 27 protrudes from the head 25 in an axial direction and this mounting pin 27 has an outer side 29 which tapers conically in an axial direction towards its end edge 28. The shape and dimension of the mounting pin 27 and the shape and dimension of the first hole 11 in the second screw-like member 5 are chosen such that they can form a press fit by compression in an axial direction, i.e. a connection which through compression permits attachment of the head member 7 and the second screw-like member 5 to each other.

The first screw-like member 4 has at least one second hole 30 which is designed to permit insertion of the rod 31 of a screw tool 32, e.g. a screw driver, into said hole 30 for securing the first screw-like member 4 to the bone in question. The second screw-like member 5 has at least one second hole 33 which is designed to permit insertion of the rod 31 of the screw tool 32 into said hole 33 for securing the second screw-like member 5 to the bone in question.

Each second hole 30 and 33 respectively, is preferably provided within the first hole 10 and 11 respectively, of each first and second screw-like member 4, 5 respectively. The rod 31 of the screw tool 32 is designed such that it can be inserted into and engage the second hole 30 and 33 respectively, by passing said rod through the first hole 10 and 11 respectively, without damaging the side walls 16 and 18 respectively, of said holes 10, 11.

Figure 2:
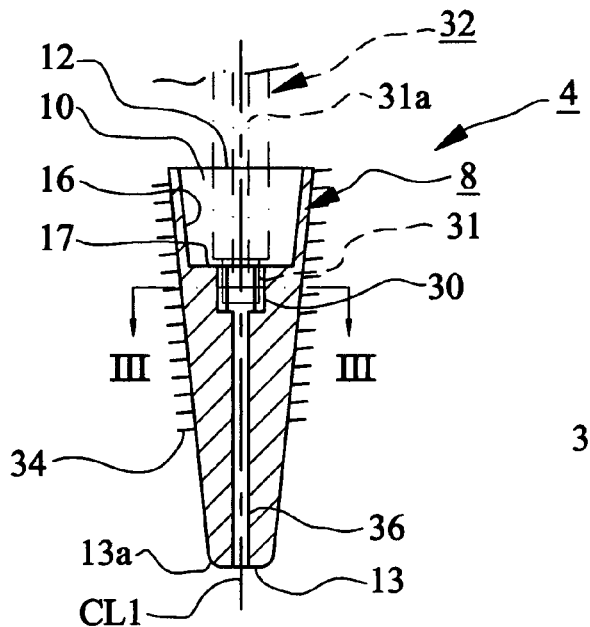
FIG. 2 is a section of a first screw-like member forming part of the wrist prosthesis of FIG. 1.
Figure 3:
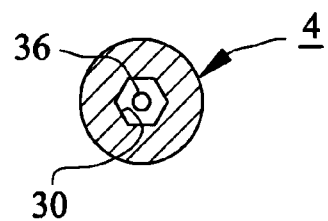
FIG. 3 is a section along the line III-III of the first screw-like member of FIG. 2.
Figure 4:
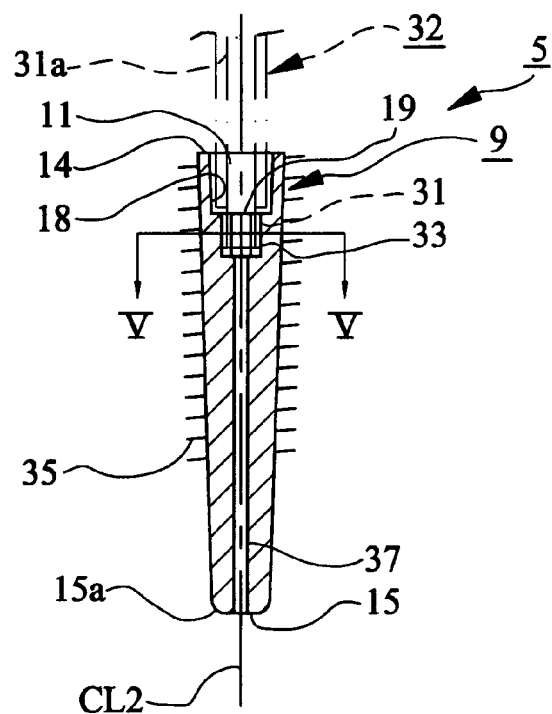
FIG. 4 is a section of a second screw-like member forming part of the wrist prosthesis of FIG. 1.
Figure 5:
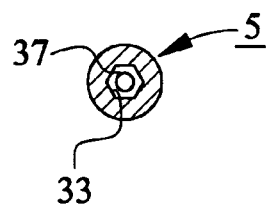
FIG. 5 is a section along the line V-V of the first screw-like member of FIG. 4.
Figure 6:
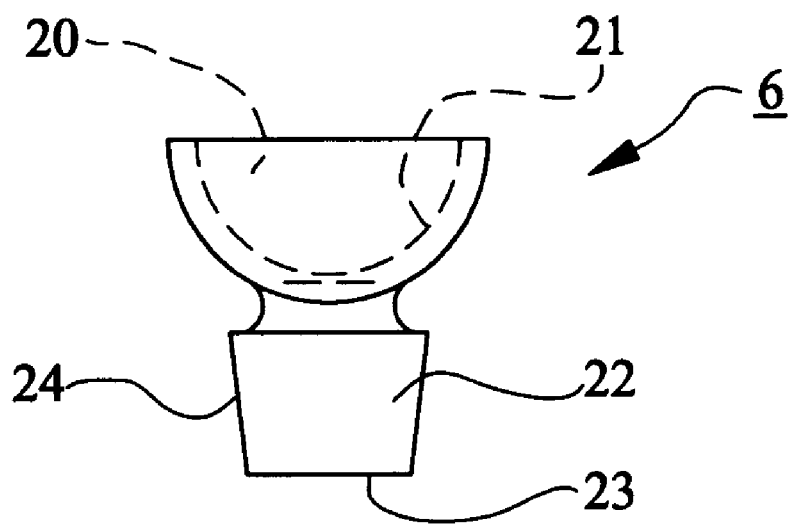
FIG. 6 is a side view of a socket member forming part of the wrist prosthesis of FIG. 1.
Figure 7:
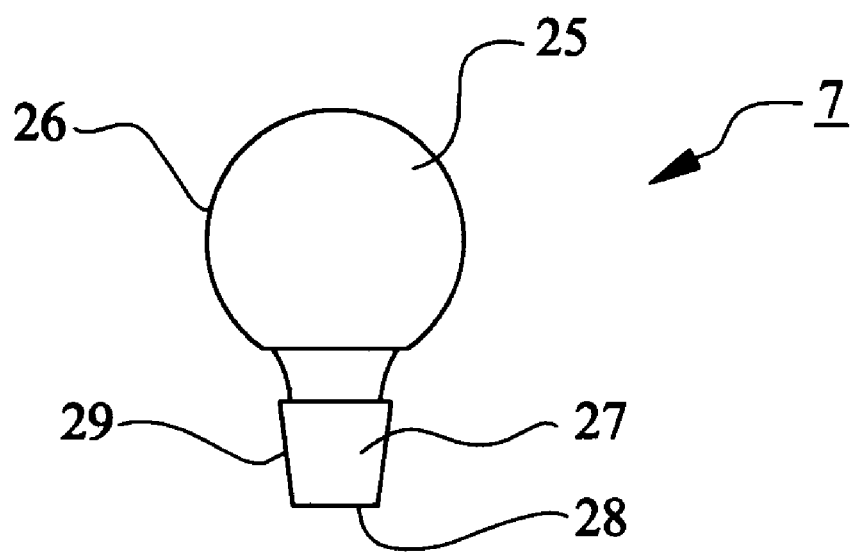
FIG. 7 is a side view of a head member forming part of the wrist prosthesis of FIG. 1.

As is illustrated in FIGS. 2 and 4, each second hole 30 and 33 respectively, may e.g. be located at the bottom 17 and 19 respectively, of the respective first hole 10, 11.

Each second hole 30 and 33 respectively, is preferably, as is the first hole 10 and 11 respectively, centered with the respective center line CL1, CL2. Furthermore, the second hole 30 and 33 respectively, may be a non-round hole, e.g. a polygonal hole, such as a hexagonal hole or similar. The rod 31 of the screw tool 32 is of course adapted to the shape of the second hole 30 and 33 respectively, such that one can turn the respective screw-like member 4, 5 by turning the screw tool 32 for screwing said screw-like members into the respective bone.

Each first and second screw-like member 4, 5 respectively, is on the outer side preferably tapering conically from the first end edge 12 and 14 respectively, in a direction towards the second end edge 13 and 15 respectively. The conical shape extends preferably, but not necessarily, the entire way between said first and second end edges 12, 14 and 13, 15 respectively. Each first and second screw-like member 4, 5 respectively, is also provided with outer threads 34 and 35 respectively, which preferably are self-tapping.

As is illustrated in the drawings, the outer threads 34 and 35 respectively, may start at the first end edge 12 and 14 respectively, and end a distance from the second end edge 13 and 15 respectively, such that the pointed end of the first and second screw-like member 4, 5 respectively, has no threads.

Each first and second screw-like member 4, 5 respectively, may be without threads at elongated parts 4a and 5a respectively, which extend in axial direction along the first and second screw-like member 4, 5 respectively, in order to divide the outer threads 34 and 35 respectively, into several, e.g. four, threaded sections.

Each first and second screw-like member 4, 5 respectively, may have an axial through hole 36 and 37 respectively, which is centered with the center line CL1 and CL2 respectively, and which is intended to permit threading of said member 4 and 5 respectively, onto a guide wire 43 which is intended to be provided at the respective bone and which is intended to guide the first and second screw-like member 4, 5 respectively, when said member shall be screwed into the respective bone.

The illustrated wrist prosthesis can be located in a wrist 38. The bones therein and in the arm and the hand are shown schematically in FIG. 1 with broken lines and these bones may be the radius 39 in the arm, one or more bones in the carpus 40, e.g. the capitate 41 and one metacarpal bone 42, e.g. metacarpal III, in the metacarpus. As is apparent from the figure, the first screw-like member 4 has been screwed into the radius 39 and this member 4 has therefore been made thicker but shorter than the second screw-like member 5 and has a larger first hole 10 than the first hole 11 of the second screw-like member 5. The second screw-like member 5 is, at the illustrated wrist 38, secured by screwing to the capitate 41 and the metacarpal bone 42.

In FIGS. 8-12, examples of how the first and second screw-like members 4, 5 can be positioned or located in the respective bone 39, 41 and 42 are shown.

Figure 8:
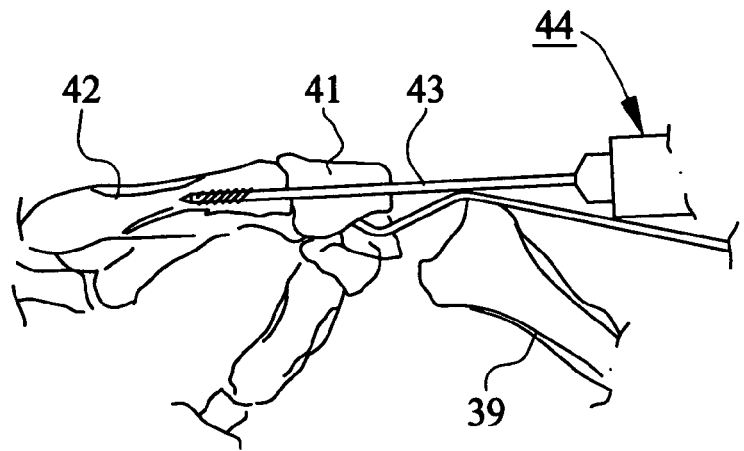
FIGS. 8-12 illustrate various moments during the positioning of screw-like members forming part of the wrist prosthesis of FIG. 1.

As is illustrated in FIG. 8, a guide wire 43 which is attached to a drill 44 is bored through the capitate 41 and into the metacarpal bone 42. Then, the drill 44 is removed while the guide wire 43 is left.

Figure 9:
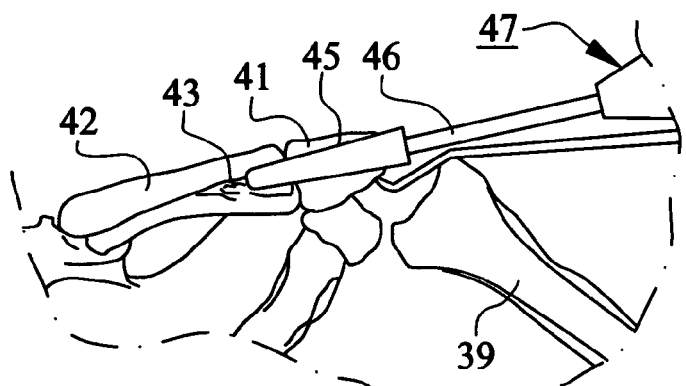

As is shown in FIG. 9, a conical drill steel 45 and a tubular bracket 46 through which the drill steel 45 is provided on a drill 47, is then threaded onto the guide wire 43 and conical holes are drilled in the capitate 41 and the metacarpal bone 42.

Figure 10:
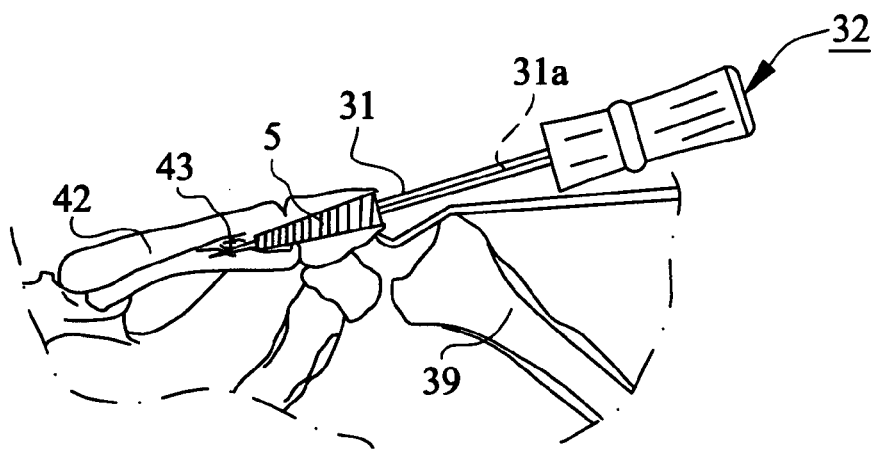

FIG. 10 illustrates how the second screw-like member 5 then is threaded onto the guide wire 43. Thereafter, the rod 31 of the screw driver 32, which is cannulated, i.e. has an elongated hole 31a, is threaded onto the guide wire 43 and into the second hole 33 of the second screw-like member 5, whereafter the screw driver 32 is turned for securing the second screw-like member 5 in the holes in the capitate 41 and the metacarpal bone 42. Then, the screw driver 32 and the guide wire 43 are removed.

Figure 11:
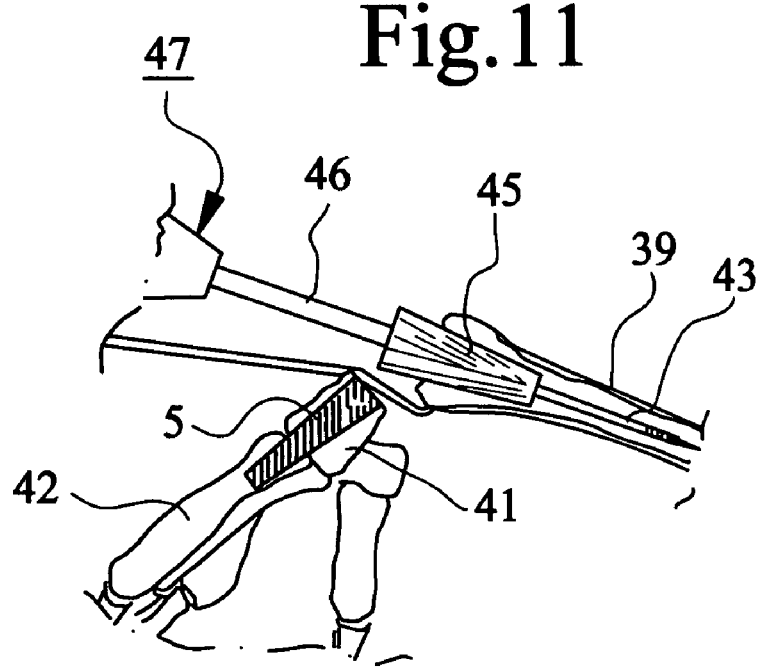
Figure 12:
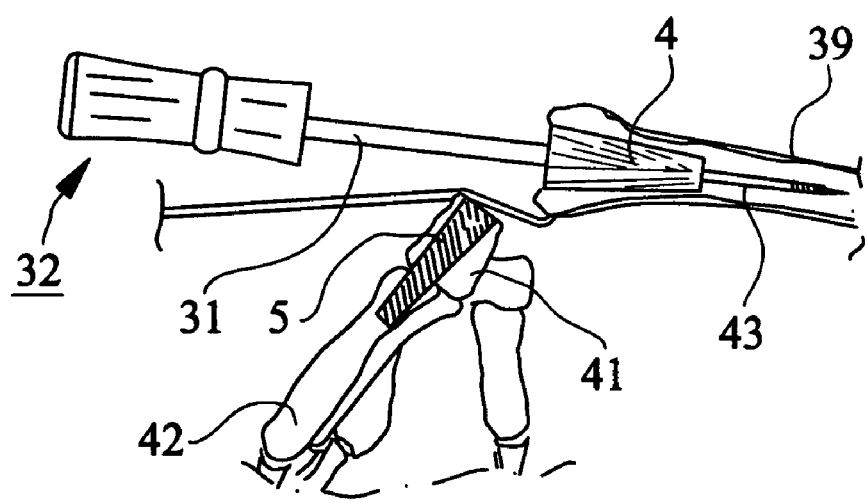

As is apparent from FIGS. 11 and 12, the procedure is the same for positioning the first screw-like member 4 at the radius 39. Thus, it is apparent from FIG. 11 that a guide wire 43 has been secured in the radius 39, that a conical drill steel 45 (which in this case is larger than the drill steel 45 of FIG. 9) has been threaded onto the guide wire 43 and that a conical hole has been bored or drilled in the radius 39 by means of the drill steel 45. In FIG. 12 it is shown that by means of the screw driver 32, the first screw-like member 4 has been secured by screwing to the radius 39, whereafter the guide wire 43 is removed therefrom.

The first and second screw-like members 4, 5 respectively, may consist of at least one material and the socket and head members 6, 7 of at least one other material. Thus, each first and second screw-like member 4, 5 respectively, may have a core of metallic material and an exterior layer of a material which is dissoluble when the first and second screw-like members 4, 5 respectively, are implanted.

Said core may preferably consist of a titanium alloy, while the dissoluble material may be or contain calcium phosphate.

The socket and head members 6, 7 may consist of a chromium-cobalt alloy.

Except for that the joint prosthesis described above is simple and easy to position, it permits rotation of the joint inter alia because the ulna can be left intact. Also, the operation can be kept small because one has to cut off only small parts of the respective bone 39; 41, 42 for attaching or securing the screw-like members 4, 5. By using the joint prosthesis instead of an arthrodesis plate, the joint can be kept movable instead of fusing the joint. If complications should occur after use of the joint prosthesis, it can be replaced by an arthrodesis plate as a secondary operation. It is also possible to screw the screw-like members 4, 5 completely or only partly into the respective bone 39; 41, 42.

The invention is not limited to the embodiment described above, but may vary within the scope of the subsequent claims. Thus, the prosthesis members can be used for other smaller joints than wrists 38, e.g. for interphalangeal joints, thumb joints, cubital joints or hallux joints. The design of the prosthesis members 2, 3 may also vary. Thus, the first holes 10, 11 in the screw-like members 4, 5 may be partly conical or eventually have another shape than conical shape and the socket and head members 6, 7 are naturally adapted thereto. The described press fit may instead be another type of coupling device, the second holes 30, 33 may have another suitable shape than described and be located in another suitable way than described. The socket and the head of the socket and head members 6, 7 may have another shape than shown and the end edges 13, 15 of the screw-like members 4, 5 may have rounded corners 13a, 13b. Finally, it should be mentioned that the screw tool 32 may be of another suitable type of screw tool than a screw driver.

The invention claimed is:

1. Joint prosthesis, comprising two prosthesis members (2, 3) which are adapted to be positioned at different bones (39, 41, 42) at a joint (38), wherein:
   each prosthesis member (2, 3) includes a first and a second screw-like member (4, 5) respectively, which are adapted to be screwed onto the respective bone (39, 41, 42),
   one prosthesis member (2) includes a member (6) having a socket and the other prosthesis member (3) includes a member (7) having a head,
   the socket member (6) has a mounting pin (22) which is insertable into a first hole (10) in the first screw-like member (4) for positioning or locating the socket member (6) thereto, and
   the head member (7) has a mounting pin (27) which is insertable into a first hole (11) in the second screw-like member (5) for positioning or locating said head member (7) thereto,
   in the first as well as in the second screw-like member (4, 5) there is provided at least one inner second hole (30 and 33 respectively) which is designed to permit insertion thereinto of a rod (31) of a screw tool (32) in order to secure by screwing the first and second screw-like member (4, 5) respectively, at the respective bone (39, 41, 42),
   the inner second hole (30 and 33 respectively) is provided in a bottom (17 and 19 respectively) of the first hole (10 and 11 respectively), and
   each first and second screw-like member (4, 5) respectively, has a through hole (36 and 37 respectively) which extends therethrough in an axial direction in order to permit threading of said first and second screw-like members (4, 5) respectively, onto a guide wire (43) which could be attached to the respective bone (39, 41, 42).

2. Joint prosthesis according to claim 1, wherein the second hole (30 and 33 respectively) is provided close to the first hole (10 and 11 respectively) of the first and second screw-like member (4, 5) respectively.

3. Joint prosthesis according to claim 1, wherein:
   the second hole (30 and 33 respectively) in the first and second screw-like member (4, 5) respectively, is provided within the first hole (10 and 11 respectively) of the first and second screw-like members (4, 5) respectively, and
   said rod (31) can be inserted into said second hole (30 and 33 respectively) by passing it through the first hole (10 and 11 respectively) of the first and second screw-like members (4, 5) respectively.

4. Joint prosthesis according to claim 1, wherein the second hole (30 and 33 respectively) is a non-round hole.

5. Joint prosthesis according to claim 4, wherein the second hole (30 and 33 respectively) is a polygonal hole.

6. Joint prosthesis according to claim 5, wherein the second hole (30 and 33 respectively) is a hexagonal hole.

7. Joint prosthesis according to claim 1, wherein the second hole (30 and 33 respectively) and the first hole (10 and 11 respectively) are centered or substantially centered with a common geometric center line (CL1 and CL2 respectively) extending through the first and second screw-like members (4, 5) respectively.

8. Joint prosthesis according to claim 1, wherein the first hole (10 and 11 respectively) in the first and second screw-like member (4, 5) respectively, and the mounting pin (22 and 27 respectively) of the socket and head members (6, 7) respectively, are designed such that the first and second screw-like members (4, 5) respectively, and the socket and head members (6, 7) respectively, are provided to define a press fit permitting the first screw-like member (4) and the socket member (6), through compression, to attach to each other, and the second screw-like member (5) and the head member (7), through compression, to attach to each other.

9. Joint prosthesis according to claim 8, wherein the first hole (10 and 11 respectively) in each first and second screw-like member (4, 5) and the mounting pins (22 and 27 respectively) of the socket and head members (6, 7) respectively, are conical.

10. Joint prosthesis according to claim 1, wherein the first and second screw-like members (4, 5) respectively, have an exteriorly conical shape and are provided with outer threads (34 and 35 respectively).

11. Joint prosthesis according to claim 10, wherein the outer threads (34 and 35 respectively) of each first and second screw-like member (4, 5) respectively, begin at a first end edge (12 and 14 respectively) thereof and end at a distance within a second end edge (13 and 15 respectively) thereof such that each first and second screw-like member (4, 5) respectively, has a pointed end without threads.

12. Joint prosthesis according to claim 10, wherein the outer threads (34 and 35 respectively) of each first and second screw-like member (4, 5) respectively, are self-tapping.

13. Joint prosthesis according to claim 10, wherein each first and second screw-like member (4, 5) respectively, has no threads at elongated parts (4a and 5a respectively) thereof, which extend in an axial direction along the first and second screw-like member (4, 5) respectively, in order to divide the outer threads (34 and 35 respectively) into several threaded sections.

14. Joint prosthesis according to claim 1, wherein the guide wire (43) is designed for guiding a conical drill steel (45) for drilling or boring a hole in the respective bone (39, 41, 42) for the first and second screw-like member (4, 5) respectively.

15. Joint prosthesis according to claim 1, wherein the head (25) of the head member (7) is spherical and that the socket member (6) has a socket (20) fitting thereto.

16. Joint prosthesis according to claim 1, wherein each first and second screw-like member (4, 5) respectively, consists of at least one material and that each socket and head member (6, 7) consists of at least one other material.

17. Joint prosthesis according to claim 1, wherein each first and second screw-like member (4, 5) respectively, has a core of metallic material and at least one exterior layer of material which is dissolved when the first and second screw-like members (4, 5) respectively, are implanted.

18. Joint prosthesis according to claim 17, wherein the metallic material in the core is a titanium alloy and that the dissoluble material is or contains calcium phosphate.

19. Joint prosthesis according to claim 1, wherein the socket and head members (6, 7) consists of a chromium-cobalt alloy.

20. Joint prosthesis according to claim 1, wherein the prosthesis members (2, 3) are designed to be used at wrists (38).

21. Joint prosthesis according to claim 20, wherein the first screw-like member (4) is designed to be screwed onto the radius (39) of the arm and the second screw-like member (5) onto at least one of the bones of the carpus (40), e.g. the capitate (41) and one metacarpal bone (42), e.g. metacarpal III, in the metacarpus.

22. Joint prosthesis according to claim 20, wherein the first screw-like member (4) is thicker, shorter and has a larger first hole (10) than the second screw-like member (5).

23. Joint prosthesis according to claim 1, wherein the prosthesis members (2, 3) are designed to be used at interphalangeal joints, thumb joints, cubital joints, hallux joints or other smaller joints than wrists.

24. A method of implanting a joint prosthesis, comprising two prosthesis members (2, 3) which are adapted to be positioned at different bones (39, 41,42) at a joint (38), wherein:
- each prosthesis member (2, 3) includes a first and a second screw-like member (4, 5) respectively, which are adapted to be screwed onto the respective bone (39; 41, 42),
- one prosthesis member (2) includes a member (6) having a socket and the other prosthesis member (3) includes a member (7) having a head,
- the socket member (6) has a mounting pin (22) which is insertable into a first hole (10) in the first screw-like member (4) for positioning or locating the socket member (6) thereto, and
- the head member (7) has a mounting pin (27) which is insertable into a first hole (11) in the second screw-like member (5) for positioning or locating said head member (7) thereto,
- in the first as well as in the second screw-like member (4, 5) there is provided at least one inner second hole (30 and 33 respectively) which is designed to permit insertion thereinto of a rod (31) of a screw tool (32) in order to secure by screwing the first and second screw-like member (4, 5) respectively, at the respective bone (39, 41,42),
- the inner second hole (30 and 33 respectively) is provided in a bottom (17 and 19 respectively) of the first hole (10 and 11 respectively), and
- each first and second screw-like member (4, 5) respectively, has a through hole (36 and 37 respectively) which extends therethrough in an axial direction in order to permit threading of said first and second screw-like members (4, 5) respectively, onto a guide wire (43) which could be attached to the respective bone (39, 41, 42),
- the method comprising the use of a screw tool for securing by screwing the first and second screw-like members (4, 5) onto different bones (39, 41, 42), wherein a rod (31) of the screw tool (32) is inserted into the second inner hole (30 and 33 respectively) in the first and second screw-like members (4, 5) respectively, such that these members can be screwed into the respective bone (39, 41, 42).

25. The method of implanting according to claim 24, wherein the rod (31) is threaded onto a guide wire (43) in order to permit securing by screwing a first and second screw-like member (4, 5) respectively, which is threaded onto the guide wire (43), into the respective bone (39, 41,42) by means of the screw tool (32).

26. The method of implanting according to claim 24, wherein a screw driver is used as the screw tool (32).

27. Joint prosthesis, comprising two prosthesis members (2, 3) which are adapted to be positioned at different bones (39, 41, 42) at a joint (38), wherein:
- each prosthesis member (2, 3) includes a first and a second screw-like member (4, 5) respectively, which are adapted to be screwed onto the respective bone (39; 41, 42),
- one prosthesis member (2) includes a member (6) having a socket and the other prosthesis member (3) includes a member (7) having a head,
- the socket member (6) has a mounting pin (22) which is insertable into a first hole (10) in the first screw-like member (4) for positioning or locating the socket member (6) thereto, and
- the head member (7) has a mounting pin (27) which is insertable into a first hole (11) in the second screw-like member (5) for positioning or locating the head member (7) thereto,
- in the first as well as in the second screw-like member (4, 5) there is provided at least one inner second hole (30 and 33 respectively) which is designed to permit insertion thereinto of a rod (31) of a screw tool (32) in order to secure by screwing the first and second screw-like member (4, 5) respectively, at the respective bone (39, 41, 42),
- the inner second hole (30 and 33 respectively) being provided within the first hole (10 and 11 respectively) in a bottom (17 and 19 respectively) of the first hole (10 and 11 respectively) of the first and second screw-like members (4, 5) respectively, the second hole (30 and 33 respectively) and the first hole (10 and 11 respectively) being centered or substantially centered with a common geometric center line (CL1 and CL2 respectively) extending through the first and second screw-like members (4, 5) respectively, the rod (31) being insertable into the second hole (30 and 33, respectively) by passing it through the first hole (10 and 11 respectively) of the first and second screw like-members (4, 5) respectively, and
- each first and second screw-like member (4, 5) respectively, having a through hole (36 and 37 respectively) which extends therethrough in an axial direction in order to permit threading of the first and second screw-like members (4, 5) respectively, onto a guide wire (43) which could be attached to the respective bone (39, 41, 42).

* * * * *